United States Patent [19]

Mandell

[11] Patent Number: 5,489,208

[45] Date of Patent: Feb. 6, 1996

[54] DENTAL BUR WITH LIQUID-COOLED TIP

[76] Inventor: Charles S. Mandell, 3220 Stirling Rd., Hollywood, Fla. 33021

[21] Appl. No.: 327,598

[22] Filed: Oct. 24, 1994

Related U.S. Application Data

[63] Continuation-in-part of Ser. No. 215,157, Mar. 21, 1994, Pat. No. 5,435,722.

[51] Int. Cl.$^6$ .................................................. A61C 3/02
[52] U.S. Cl. ............................................. 433/165; 433/82
[58] Field of Search ............................ 433/82, 104, 165, 433/166; 408/57, 59; 51/356

[56] References Cited

U.S. PATENT DOCUMENTS

| | | | |
|---|---|---|---|
| 2,442,033 | 5/1948 | Brantly et al. | 433/165 |
| 2,799,934 | 7/1957 | Kern | 433/82 |
| 4,601,661 | 7/1986 | Du Bé et al. | 433/134 |

*Primary Examiner*—Cary E. O'Connor
*Attorney, Agent, or Firm*—Oltman and Flynn

[57] ABSTRACT

According to the invention, there is provided an elongated liquid-cooled dental bur having a long direction, a proximal part adapted to be inserted into a drive device connected with a source of cooling fluid, a distal part having a cutting tip, a first channel in the proximal part fluidly communicating with the source of cooling fluid and at least one orifice extending from the first channel directed at the cutting tip for directing a spray of cooling liquid at the cutting tip, a cutting tip outer surface, a second channel fluidly communicating with the source of cooling fluid and extending longitudinally through the distal part and into the cutting tip, a discharge port extending through the tip outer surface for cooling the cutting tip. The dental bur may further include a collar radially extending from the proximal part having a circumference, wherein the orifice is disposed in the collar proximal to the circumference, and wherein the collar has an end surface disposed transversely to the long direction facing the distal part, and the orifice is disposed in the end surface. The cutting tip has a substantially cylindrical shape or a tapered shape.

8 Claims, 1 Drawing Sheet

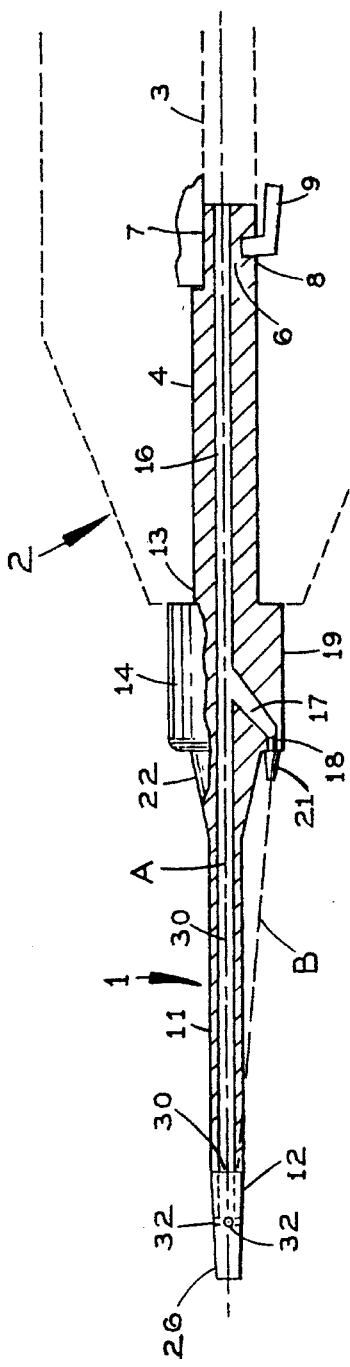
FIG. 1
FIG. 1a
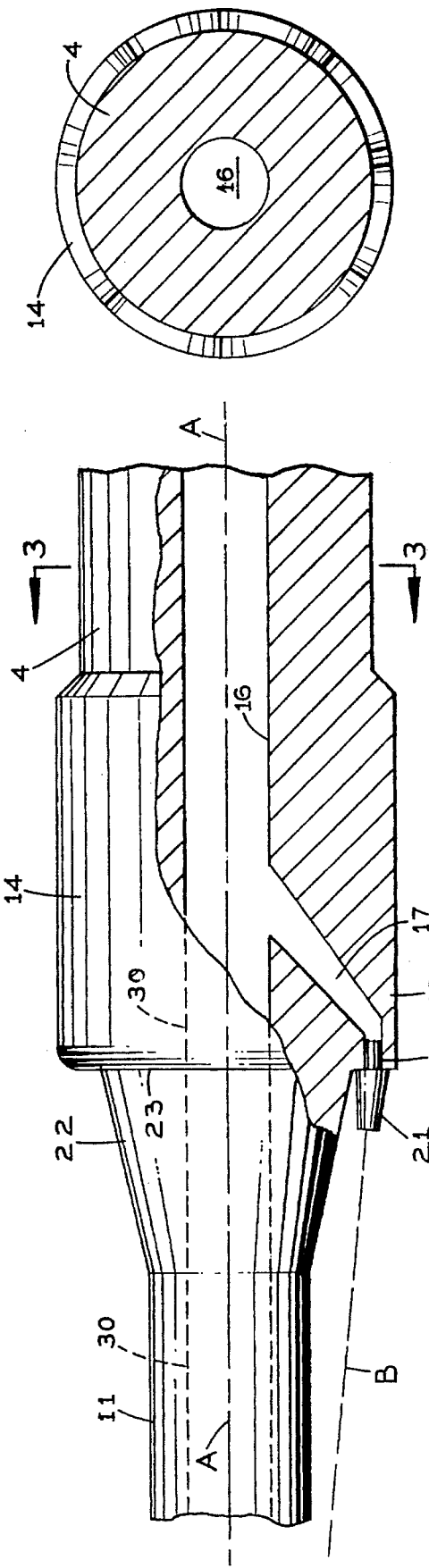
FIG. 3
FIG. 2

DENTAL BUR WITH LIQUID-COOLED TIP

FILING HISTORY

This application is a continuation-in-part of application Ser. No. 08/215,157 filed on Mar. 21, 1994 now U.S. Pat. No. 5,435,722.

BACKGROUND OF THE INVENTION

1. Field of the Invention

The invention relates to a dental bur adapted to be cooled with a cooling liquid, and more particularly to a water-cooled dental bur having a proximal part for insertion into a drive device and a distal part with a cutting tip, and having an internal water channel which divides into a lateral channel terminating in a water discharge aperture directing cooling water at the cutting tip and an axial channel extending longitudinally through the distal part and terminating in a radial discharge port in the cutting tip.

2. Description of the Prior Art

It is known that the process of drilling and cutting bone with the dental cutting tool known as a "dental bur" creates a great deal of heat. The heat generated by the bur desiccates the bone and causes pain and discomfort to the patient. It is therefore desirable to apply cooling to the bur and the bone during the drilling and cutting process.

It is known from the prior art to provide a water channel in a dental bur, as shown in U.S. Pat. No. 3,393,452, which shows a dental bur having a bore through its shank and through the cutting tip of the bur extending to its distal end for admitting cooling water to the area of the tooth being drilled or cut. This single cooling water delivery means can be inadequate to the task. Burs of such small diameter are often required for drilling and cutting bone. U.S. Pat. No. 5,100,322 shows a water-cooled dental tool which has an internal hollow space and holes cut transversely through the cutting tip of the tool for admitting a stream of liquid or air for cooling the drilling operation. The dental bur according to the last mentioned patent relies on only cooling liquid sprayed against the exterior of the cutting tool, which is often inadequate.

It is accordingly an object of the present invention to provide a liquid-cooled dental bur which does not have the drawbacks of the known dental burs, and which provides effective cooling also for dental burs of quite small diameters.

Further objects and advantages of this invention will be apparent from the following detailed description of a presently preferred embodiment which is illustrated schematically in the accompanying drawings.

SUMMARY OF THE INVENTION

According to the invention, there is provided an elongated liquid-cooled dental bur having a long direction, a proximal part adapted to be inserted into a drive device connected with a source of cooling fluid, a distal part having a cutting tip, a channel in the proximal part fluidly communicating with the source of cooling fluid and at least one orifice extending from the channel directed at the cutting tip for directing a spray of cooling liquid at the cutting tip, and further including a collar radially extending from the proximal part having a circumference, wherein the orifice is disposed in the collar proximal to the circumference, and wherein the collar has an end surface disposed transversely to the long direction facing the distal part, and the orifice is disposed in the end surface, wherein a liquid-cooled dental bur is provided in which the cutting tip includes a tip outer surface, additionally including a second channel fluidly communicating with the source of cooling fluid and extending longitudinally through the distal part and into the cutting tip, a discharge port extending through the tip outer surface for cooling the cutting tip. The cutting tip may be substantially cylindrically shaped or tapered.

According to a further feature the proximal end part is shaped as an elongate cylinder, and the channel is shaped as a central bore in the cylinder and the proximal end part has a facet substantially parallel with the long direction for rotationally locking the bur in the drive device.

According to still another feature, the end part has a radial recess for axially locking the bur in the drive device.

As a still further feature, the cooling fluid is composed substantially of water.

BRIEF DESCRIPTION OF THE DRAWINGS

FIG. 1 is a diagrammatic, part cross-sectional view of a dental bur according to the invention, illustrating the cutting tip, distal cooling water delivery channel and laterally oriented cutting tip radial discharge port;

FIG. 1a is a fragmentary view of an alternative cutting tip.

FIG. 2 is a fragmentary, part cross-sectional view of the central part of the dental bur according to the invention; and FIG. 3 is a cross-sectional view seen along the line 3—3 of FIG. 2.

Before explaining the disclosed embodiments of the present invention in detail it is to be understood that the invention is not limited in its application to the details of the particular arrangements shown since the invention is capable of other embodiments. Also, the terminology used herein is for the purpose of description and not of limitation.

DESCRIPTION OF THE PREFERRED EMBODIMENTS

In FIG. 1 a dental bur generally at 1 is shown inserted in a drive device, generally at 2, shown in phantom lines. The drive device has an internal central channel 3 which leads to a source of cooling liquid under a given amount of pressure.

The dental bur 1 is elongated in a long direction indicated by a dash-dot line A, and is composed of a proximal part 4 and a distal end 11 having a cutting tip 12. The cutting tip 12 may for example have a diameter of 1.6 mm with an abrasive or cutting surface. The proximal part is insertable in a drive device 2, and has at its end 6 a facet 7, which is substantially parallel with the long direction A. The facet 7 mates with a corresponding flat surface in drive device 2 to provide a rotational lock on the bur 1.

The proximal part 6 also has an indentation or groove 8 which mates with a releasable latch 9 in the drive device 2, and provides axial lock of the dental bur. The proximal part 4 is advantageously of cylindrical shape in which case the dash-dot line A indicates the axis of the bur.

The proximal part 4 expands at its end 13 facing away from the drive device 2 into a collar 14 at a somewhat greater diameter of the proximal part 4. The proximal part 4 has an internal bore or channel 16 which communicates at its proximal end with the central channel 3 of the drive device 2. The channel 16 extends through the collar 14 and then divides into two branches. One branch deviates in the collar away from the axis A via a short channel section 17 to communicate with an orifice 18 disposed proximal to the circumference 19 of the collar 14, which in turn communicates with a small spout or jet 21 which has an axis shown by the dash-dot line B, that is converging with the axis A at a point near the cutting tip 12, so as to direct a stream of cooling fluid ejected from the jet 21 at the cutting tip and the cutting area of the bone being cut.

The second branch is an axial distal delivery channel 30 extending into cutting tip 12, as illustrated, which discharges through a laterally directed radial discharge port 32, to cool cutting tip 12. Port 32 opens out through a cutting tip 12 to outer surface 26. It is contemplated that more than one radial discharge port 32 may be provided in cutting tip 12. Cooling water discharge through cutting tip 12 also cools and lubricates outer surface 26 and the surface against which cutting tip 12 bears during bur operation. This distal delivery of cooling water is provided in addition to jet 21 water delivery, and is contemplated for any cutting tip 12 shape. One cutting tip 12 shape is tapered (FIG. 1) and another is cylindrical (FIG. 1a). Cutting tip 12 is preferably, though not necessarily, 1.6 mm. in diameter. The tapered version tapers from 1.6 m.m. to 1.3 m.m.

FIG. 2 shows in a cross-sectional enlarged view the details described above, including the channel 16 in the proximal part 4 and the collar 14, which deviates as channel section 17 and communicates with the orifice 18 and the jet 21.

FIG. 3 is an end view taken along line 3—3 of FIG. 2, showing the circumference of the collar 14, the proximal part 4 in cross-section and the internal channel 16 of the proximal part 4.

It follows that more than one orifice 18 may be provided, in which case the orifices are arranged equidistantly about the circumference of the collar 14. FIG. 3 shows the collar 14 extending beyond the root 22 of the distal part 11, forming a shoulder 23 which lies in a plane perpendicular to the axis A, facing the cutting tip 12 of the dental bur. The root 22 is advantageously formed as a conical or flared part of the distal part 11.

I claim:

1. An elongated liquid-cooled dental bur having a long direction comprising:

a proximal part adapted to be inserted into a drive device connected with a source of cooling fluid, a distal part having a distal part longitudinal axis and having a cutting tip with a tip outer surface, a first channel in said proximal part fluidly communicating with said source of cooling fluid and at least one orifice extending from said first channel directed at said cutting tip for directing a spray of cooling fluid at said cutting tip, a collar radially extending from said proximal part having a circumference, wherein said orifice is disposed in said collar proximal to said circumference, a second channel fluidly communicating with said source of cooling fluid and extending longitudinally through said distal part and into said cutting tip, a discharge port extending substantially radially from said distal part longitudinal axis and through said tip outer surface for cooling said cutting tip.

2. A liquid-cooled dental bur according to claim 1, wherein said collar has an end surface disposed transversely to said long direction and facing said distal part, and said orifice is disposed in said end surface.

3. A liquid-cooled dental bur according to claim 1, wherein said proximal part is shaped as an elongate cylinder, and said first channel is shaped as a central bore in said cylinder.

4. A liquid-cooled dental bur according to claim 3, wherein said proximal part has a facet substantially parallel with said long direction for rotationally locking said bur in said drive device.

5. A liquid-cooled dental bur according to claim 3, wherein said proximal part has a radial recess for axially locking said bur in said drive device.

6. A liquid-cooled dental bur according to claim 1, wherein said cutting tip is substantially cylindrically shaped.

7. A liquid-cooled dental bur according to claim 1, wherein said cooling fluid is composed substantially of water.

8. A liquid cooled dental bur according to claim 1, wherein said cutting tip is tapered.

\* \* \* \* \*